United States Patent [19]

Iimuro et al.

[11] Patent Number: 4,935,553
[45] Date of Patent: Jun. 19, 1990

[54] PROCESS FOR PREPARING BISPHENOL A

[75] Inventors: Shigeru Iimuro; Yoshio Morimoto; Takashi Kitamura, all of Aichi, Japan

[73] Assignee: Mitsui Toatsu Chemicals, Inc., Tokyo, Japan

[21] Appl. No.: 294,120

[22] Filed: Jan. 6, 1989

[30] Foreign Application Priority Data

Jan. 8, 1988 [JP] Japan .................................. 63-001348

[51] Int. Cl.$^5$ ........................ C07C 37/20; C07C 39/16
[52] U.S. Cl. .................................... 568/727; 568/722; 568/728
[58] Field of Search ........................ 568/727, 728, 922

[56] References Cited

U.S. PATENT DOCUMENTS

| 2,036,272 | 5/1960 | Bender | 568/727 |
| 2,730,553 | 1/1953 | Williamson | 568/727 |
| 2,775,620 | 12/1956 | Williamson | 568/727 |
| 2,791,616 | 3/1957 | Luten, Jr. | 568/727 |

FOREIGN PATENT DOCUMENTS

| 275367 | 8/1941 | Japan | 568/727 |
| 407186 | 2/1962 | Japan | 56/727 |
| 0062543 | 4/1984 | Japan | 568/727 |
| 61-78741 | 4/1986 | Japan | 568/727 |
| 785079 | 10/1957 | United Kingdom | 568/727 |

Primary Examiner—Werren B. Lone
Attorney, Agent, or Firm—Burns, Doane, Swecker & Mathis

[57] ABSTRACT

A process for preparing high purity bisphenol A comprising feeding continuously phenol and acetone in the presence of a hydrochloric acid catalyst into a first stage reactor and reacting phenol and acetone in the range of 20-60 mol % of acetone conversion and continuously removing the first reaction product from the first stage reactor. The first reaction product is fed into a second stage reactor and the reaction of phenol and acetone is completed to obtain a second reaction product from which bisphenol A is recovered.

3 Claims, No Drawings

PROCESS FOR PREPARING BISPHENOL A

BACKGROUND OF THE INVENTION

The present invention relates to a process for preparing high purity 2,2-bis(4-hydroxyphenyl)propane (hereinafter referred to as bisphenol A).

Bisphenol A is used as a raw material for polycarbonate resins or epoxy resins. Colorless and high purity bisphenol A is required for polycarbonate resins in particular.

Bisphenol A is prepared from acetone and excess phenol in the presence of an acidic catalyst, and in some cases by the addition of a co-catalyst such as sulfur compounds. The reaction mixture contains the catalyst, unreacted acetone, unreacted phenol, water and other by-products of the reaction.

The by-products are mainly composed of 2-(2-hydroxyphenyl)-2-(4-hydroxyphenyl) propane (hereinafter referred to as o,p' isomer). The by-products also contain Dianin's compound, trisphenol, polyphenol and undesirable colored substances. These by-products deteriorate the properties of resins prepared from bisphenol A.

Hydrochloric acid or strongly acidic ion exchange resins are known as a catalyst of this reaction. In the use of hydrochloric acid, an adduct of bisphenol A and phenol is precipitated while the reaction proceeds at a low temperature. At the same time, o,p' isomer by-products are isomerized to p,p' isomer (bisphenol A) and consequently, the amount of o,p' isomer can be reduced.

On the other hand, Dianin's compound can be reduced by adding 3% or more of water by the method described in Japanese Patent Publication 40-7186 or by the addition of mercapto-compounds as described in Japanese Patent Publication No. 27-5367. However, adding a large amount of water requires many steps, such as dehydration, and the separation and recovery of hydrochloric acid after reaction. Adding a mercapto-compound also requires complicated separation steps and results in the emission of an undesired odor. These two methods are, therefore, not practically used on an industrial scale.

Dianin's compound can also be reduced using an excess of phenol with respect to acetone. However, o,p' isomer increases with a decrease in the adduct of bisphenol-A and phenol. Furthermore, the bisphenol A must be isolated from the other substances, such as the excess phenol, present in large quantities in the reaction mixture.

Continuous reaction using an excess of phenol results in an increasing amount of the o,p' isomer. On the other hand, in a batch method, the amount of Dianin's compound increases due to the high initial concentration of acetone.

When a strongly acidic ion exchange resin is used, many impurities are produced. However, Dianin's compound is greatly reduced when a part of functional groups of the resin are modified by compounds having a mercapto-group such as mercaptoalkyl amine.

When an ion exchange resin catalyst is used, the o,p' isomer is produced to a much greater extent than when a hydrochloric acid catalyst is used because the procedure of crystallizing the adduct of phenol and bisphenol A cannot be employed.

In addition, in case of the ion exchange resin catalyst, acetone cannot be fully converted due to the water formed in the reaction as described in Japanese Patent Publication Kokai No. 61-78741. A batch method requires dehydration of the resin at each reaction, while a continuous reaction requires an enormous amount of resin for advancing the conversion to a significant extent. When acetone is isolated and recovered from water, a corrosion problem in the case of use of hydrochloric acid is not encountered. However, for isolating acetone from water and recovering the acetone, significant facilities and costs are required. Additionally, since a cation exchange resin catalyst is essentially a solid, the preparation of bisphenol A in phenol having limited solubility cannot be carried out in a high concentration, so that substantial amounts of energy and services are required for obtaining end product.

Thus, each of the conventional processes for preparing bisphenol A can reduce specific impurities, but cannot simultaneously reduce typical two impurities: o,p' isomer and Dianin's compound to a satisfactory extent.

SUMMARY OF THE INVENTION

One object of this invention is to produce a process for preparing high purity bisphenol A by decreasing the production of by-products and impurities and by simplifying the purification treatment as much as possible.

The inventors have conducted an extensive investigation in order to achieve the above stated objects and, as a result, have found that the objects of the present invention can be achieved by conducting the reaction in two stages; one continuous and one batch.

In accordance with the present invention, there is provided a process for preparing bisphenol A comprising:

(a) continuously feeding phenol, acetone, and hydrogen chloride or hydrochloric acid into a first stage reactor and reacting phenol and acetone in the range of 20–60 mol% of acetone conversion to obtain a first reaction product;

(b) continuously removing the first reaction product from the first stage reactor;

(c) feeding said first reaction product and hydrogen chloride or hydrochloric acid into a second stage reactor which is operated batchwise and completing the reaction of phenol and acetone to obtain a second reaction product; and (d) recovering bisphenol A from said second reaction product.

DETAILED DESCRIPTION OF THE INVENTION

According to the process of this invention, 4–12 mols of phenol are usually reacted with 1 mol of acetone substantially without using a solvent as the third component. In this case, a small amount of water or hydrochloric acid may be added in order to accelerate the reaction.

The total amount of acetone may be fed into the first stage reactor which is operated continuously. Alternatively, a part of the acetone may also be fed into the second stage reactor which is operated on a batch basis. The reaction in each stage may be conducted in several reactors, (in series or parallel). In a preferred embodiment, the reaction products are fed in order from the reactor of continuous type to a plurality of reactors of the batch type.

The reactor may be saturated with hydrogen chloride before the reaction. It may also be continuously fed into the reactor during the reaction. It is preferably fed before and after reaction because of heat developed from the absorption of hydrogen chloride, the heat of reaction, and heat developed by depositing the adduct of phenol and bisphenol A. The heat developed by the reaction is removed, such as by heat exchangers, to control the reaction temperature in the prescribed range.

The reaction in the first stage is conducted in a reactor which is operated continuously. This reaction is usually conducted under pressures from normal pressure to 5KG/cm$^2$ at 30–100° C., preferably 40–70° C.

When the reaction temperature is lower than 30° C., the reaction rate decreases. When the reaction temperature is higher than 100° C., by-products are produced in large quantities. The reaction time depends upon the molar ratio of acetone to phenol and the reaction temperature. The reaction mixtures are, preferably, fed to a second stage reactor before the adduct of phenol and bisphenol A is deposited. That is, before the solubility of the adduct reaches the saturation point. The mean retention time required for the saturation is approximately 1.4 hours when the molar ratio of phenol to acetone is seven and the reaction temperature is 40° C., and approximately 1.8 hours when the molar ratio is six and the reaction temperature is 55° C.

When the adduct reaches the saturation point, the crystals are deposited rapidly from the reaction mixture so that the transfer of the reaction slurry becomes difficult and therefore, it is necessary to exactly control an acetone conversion in the first stage reactor.

If the acetone conversion in the first stage reactor is too low, the initial concentration of acetone in the second stage reactor is increased and the result is similar to when the total amount of acetone is converted in the reactor of batch type, i.e., an increase of Dianin's compound. Also, if the acetone conversion is too high, a continuous operation is difficult because the reaction mixtures cannot be transferred to next the second stage reactor due to the deposition of the adduct crystals, the adhesion of the crystals to the wall of the reactor, and the growth of the crystals. It is therefore preferred that the acetone conversion be 20–60% in the first stage reactor.

By using a continuous process in the first stage, the molar ratio of phenol to acetone can be substantially increased. Thus, the formation of Dianin's compound is remarkably reduced when compared with a batch reaction in the same molar ratio.

The reaction in the second stage can be conducted by conventional methods except that the reaction mixture from the first stage is fed as a batch of the raw material. The reaction is conducted at 30–85° C., preferably 35–60° C. under agitation.

The adduct crystals are deposited as the reaction proceeds. At the same time, o,p' isomer in the reaction solution is isomerized to the corresponding p,p'-isomer (bisphenol A), thereby decreasing the ratio of o,p'-isomer to bisphenol A in the reaction system. Decreasing the final reaction temperature to 35–45° C. permits more effective isomerization. Only a small amount of Dianin's compound is produced even at the time of completion of the reaction in the second stage because the production of Dianin's compound is inhibited in the first stage reactor.

Bisphenol A is obtained by removing water, the catalyst and excess phenol from the reaction mixture. This product, as is, may be subjected to further processing steps in order to obtain granules, flakes and other forms as the final product. Alternatively, this bisphenol A may be subjected to a purification procedure, followed by processing steps to obtain a final product. For example, according to a conventional purification procedure, the adduct of bisphenol A and phenol is precipitated and thereafter, phenol is removed, for example by distillation to obtain colorless and high purity bisphenol A.

EXAMPLES

This invention will be hereinafter be described in detail with respect to examples and comparative examples. The analysis of acetone is in accordance with potentiometric titration and the analysis of o,p' isomer and Dianin's compound are in accordance with gas chromatography.

Example 1

Acetone at a rate of 58 kg/hr was added to 564 kg/hr of phenol and these materials were fed continuously into a first stage reactor controlled at 50° C. while continuously introducing 5 kg/hr of hydrogen chloride gas into the first stage reactor. The reaction mixture was continuously removed after 1.5 hours of mean retention time. The reaction mixture had an acetone conversion of 55% and contained o,p' isomer of 3.2 wt% (to bisphenol A) and Dianin's compound of 0.3 wt % (to bisphenol A). The reaction mixture was fed into a second stage reactor (internal volume: 1.2 m$^3$) over 1.2 hours.

The second stage reaction was started while blowing 5 kg/hr of hydrogen chloride gas into the second stage reactor and stirring the second stage reactor, and completed after 7 hours. The reaction temperature was 60° C. at maximum and 45° C. at the completion of the reaction. When the slurry of the reaction mixture was analyzed, o,p'-isomer and Dianin's compound were 1.5 wt% and 0.4 wt% to bisphenol A, respectively.

Example 2

Acetone at a rate of 58 kg/hr was added to 564 kg/hr of phenol, and these materials were fed continuously into the first stage reactor controlled at 50° C. while introducing 5 kg/hr of hydrogen chloride gas into the first stage reactor. The reaction mixture was continuously removed after 0.8 hour of mean retention time. Acetone conversion was 25% and the reaction mixture contained o,p' isomer of 4.5 wt% to bisphenol A and 0.2 wt% of Dianin's compound with respect to bisphenol A.

The reaction mixture was fed into a second stage reactor (internal volume: 1.2 m$^3$) over 1.2 hours. The second stage reaction was started by introducing 5 kg/hr of hydrogen chloride gas into the second stage reactor and stirring the second stage reactor and the reaction was completed after 9 hours. When the reaction mixture was analyzed, the o,p' isomer and Dianin's compound were 1.5 wt% and 0.5 wt% to bisphenol A, respectively.

Comparative Example 1

Acetone at a rate of 58 kg/hr was added to 564 kg/hr of phenol and these materials were fed continuously into the first stage reactor controlled at 50° C. while introducing 5 kg/hr of hydrogen chloride gas into the first stage reactor. The reaction mixture was continuously removed after 2.5 hours of mean retention time. However, crystals had begun to grow on the inside wall of the first stage reactor 4 hours after the operation had started. Because pipes for feeding were clogged after 7 hours, continuously operation could not be carried out. Acetone conversion was 65% until the reaction was stopped. The reaction mixture contained o,p' isomer of 4.0 wt% to bisphenol A.

Comparative Example 2

A reaction was carried out similar to Example 1 except that the mixture of phenol and acetone was directly fed into the second stage reactor, without being fed into the first stage reactor. The amount of hydrogen chloride gas fed was 10 kg/hr. Acetone conversion was 99.0% after 8 hours. The reaction mixture contained o,p' isomer of 1.6 wt% to bisphenol A and 0.7 wt% of Dianin's compound to bisphenol A. After 10 hours, acetone conversion was 99.5% and the reaction mixture contained o,p' isomer of 1.5 wt% to bisphenol A and 0.8 wt% of Dianin's compound to bisphenol A.

As can be understood from the foregoing Examples and Comparative Examples, the present invention results in a significant decrease in by-products when compared with methods using one conventional reactor operated in the batch method or several reactors operated continuously. High purity bisphenol A can very readily be obtained by isolating bisphenol A from the reaction mixture thus obtained according to conventional recovery methods.

We claim:
1. A process for preparing bisphenol A comprising
    (a) continuously feeding phenol, acetone and hydrogen chloride or hydrochloric acid into a first stage reactor maintained at a temperature of 30 to 100° C. and reacting phenol with acetone in the range of 20–60 mol% of acetone conversion to obtain a first reaction product;
    (b) continuously removing the first reaction product from the first stage reactor;
    (c) feeding a batch of said first reaction product maintained at a temperature of 30 to 85° C., thereafter feeding hydrogen chloride or hydrochloric acid into the second reactor and comprising the reaction of phenol with acetone to obtain a second reaction product as a slurry including adduct crystals of bisphenol A with phenol; and
    (d) recovering bisphenol A from said second reaction product.
2. The process of claim 1 wherein the molar ratio of phenol to acetone fed into the first stage reactor is 4:1 to 12:1.
3. The process of claim 1 wherein the second stage reactor comprises a plurality of reactors which are operated batchwise.

* * * * *

UNITED STATES PATENT AND TRADEMARK OFFICE
CERTIFICATE OF CORRECTION

PATENT NO.  : 4,935,553
DATED       : June 19, 1990
INVENTOR(S) : Shigeru IIMURO et al It is certified that error appears in the above-identified patent and that said Letters Patent is hereby corrected as shown below:

In the Claims:

In Claim 3, line 3, after "batchwise" insert --and independently--.

Signed and Sealed this

Thirty-first Day of December, 1991

Attest:

HARRY F. MANBECK, JR.

*Attesting Officer*  *Commissioner of Patents and Trademarks*